(12) United States Patent
Hung

(10) Patent No.: US 6,294,666 B1
(45) Date of Patent: Sep. 25, 2001

(54) METHODS OF PREPARING OPTICALLY PURE SUGARS

(75) Inventor: Shang-Cheng Hung, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/411,188

(22) Filed: Oct. 1, 1999

(51) Int. Cl.[7] .......................... C07H 17/04; C07D 317/06
(52) U.S. Cl. ..................... 536/124; 536/4.1; 549/31; 549/59
(58) Field of Search .................. 536/4.1, 84, 93, 536/124; 549/31, 59

(56) References Cited

PUBLICATIONS

Baggett, N. et al "Synthesis of L–iduronic acid derivatives by epimerisation of anancomeric D–glucuronic acid analogues" Carbohyd. Res. 1982, vol. 108, pp. 59–70.*
Alper et al., "Probing the Specificity of Aminoglycoside–Ribosomal RNA Interactions with Designed Synthetic Analogs", J. Am. Chem. Soc. 120:1965–1978, 1998.
Baggett et al., "Methyl Ethers of 1,6–Anhydro–β–L–Idopyranose 2,4–Di–O–methyl and 3-0–Methyl Ethers of 1,6–Anhydro–β–L–idopyranose", Journal of Organic Chemistry 28:1845–1847, 1963.
Barnes et al., Higher–Carbon Sugars. Part 13. The Catalytic Osmylation of Some α, β–Un–saturated Octuronic Acid Derivatives and a synthesis of (meso)–threo–gluco–Octitol, J. Chem. Soc. Perkin Trans 1:1483–1489, 1989.
Bazin et al., "Regio and Steroselective Conversion of Δ[4]–Uronic Acids to L–Ido– and D–Glucopyranosiduronic Acids", Tetrahedron Letters 38:923–926, 1997.
Bazin et al., "Regio– and Stereoselective Synthesis of β–D–Gluco–, α–L–Ido–, and α–L–Altropyranosiduronic Acids from Δ[4]–Uronates", J. Org. Chem 64:144–152, 1999.
Blanc–Muesser et al., "[24]L–Idose and L–Iduronic Acid", Methods in Carbohydrate Chemistry VIII:177–183, 1980.
van Boechel et al., "Synthesis of a Pentasaccharide Corresponding to the Antithrombin III Binding Fragment of Heparin", J. Carbohydrate Chemistry 4:293–321, 1995.
van Boeckel et al., "The Unique Antithrombin III Binding Domain of Heparin: A Lead to New Synthetic Antithrombotics", Angewandte Chemie International Edition in English 32:1671–1690, 1993.
Brimacombe et al., "Nucleophilic Displacement Reactions in Carbohydrates. Part XV. Displacements with 1,2: 5,6–Di–O–isopropylidene–3–O–p–tolylsulphony–β–L–talofuranose", J. Chem. Soc. 1632–1635, 1970.
Chalk et al., "conditions for Neighboring–Group Participation in Displacement Rections of 5–O–Sulfonyl–D–Glucofuranose Derivatives", Carbohydrate Research 20:151–164, 1971.
Chiba et al., "Application of a Radical Reaction to the Synthesis L–Iduronic Acid Derivatives From D–Glucuronic Analogues", Carbohydrate Research 151:379–389, 1986.

Chiba et al., "Chemical Systhesis of L–Iduronic Acid–Containing Di–Saccharidic Fragments of Heparin", Carbohydrate Research 174:253–264, 1988.
Csuk et al., "A Facile Synthesis of 1,2–O–Isopropylidene–β–L–Idofuranurono–6,3–Lactone", Tetrahedron Letters 21:2135–2136, 1980.
Dondoni et al., "Carbohydrate Homologation by the use of 2–(Trimethylsilyl)thiazole. Preparative Scale Synthesis of Rare Sugars: L–Gulose, L–Idose, and the Disaccharide . . . ", J. Org. Chem. 62–6261–6267, 1997.
Driver et al., "Septanose Carbohydrates. III Oxidation–Reduction Products from 1,2:3, 4–Di–O–isopropylidene–α–D–gluco–septanose: Preparation of L–Idose Derivatives", Aust. J. Chem. 43:2063–2081, 1990.
Fourmy et al., "Structure of the A Site of Escherichia coli 16S Ribosoma RNA Complexed with an Aminoglycoside Antibiotic", Science 274:1367–1371, 1996.
Hodosi et al., "The Mechanism of the Hydroxyl→Halogen Exchange Reaction in the Presence of Triphenylphosphine N–bromosuccinimide, and N,N–dimethylformamide: application . . . ", Carbohydrate Research 230:327–342, 1992.
Hughes et al., "1,2:3,5–Di, and 1,2:5, 6–Di–O–Isopropylidene–β–L–Idofu–Ranoses; and Example of 1,3–Dioxolane–1,3–Dioxane Isomerisation", Carbohydrate Research 101:221–229, 1982.
Jacquinet et al., "Synthesis of Heparin Fragments, a Chemical Synthesis of the Trisaccharide O–(2–Deoxy–2–Sulfamido–3,6–Di–O–Sulfo . . . ", Carbohydrate Research 130:221–241, 1984.
Kiss et al., "Synthesis of Heparin Saccharides—V Anomeric O–Benzyl Derivatives of L–Idopyranosyluronic Acid", Tetrahedron 32:1399–1402, 1976.
Lindalh, "Heparan Sulfate—A Polyanion With Multiple Messages", Pure & Appl. Chem. 69:1897–1902, 1997.

(List continued on next page.)

*Primary Examiner*—Kathleen K. Fonda
*Assistant Examiner*—Leigh C Maier
(74) *Attorney, Agent, or Firm*—Fish & Richardson P.C.

(57) ABSTRACT

The invention relates to a method of preparing a compound of the following formula:

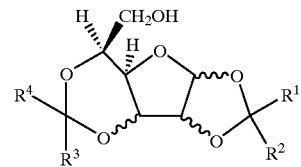

wherein each of $R^1$, $R^2$, $R^3$, and $R^4$, independently, is hydrogen, alkyl, cycloalkyl, heterocycloalkyl, alkoxy, aryl, heteroaryl, aralkyl, heteroaralkyl, haloalkyl, or alkyloxyalkyl, provided that $R^1$ and $R^2$, optionally form a keto or, with the carbon atom to which they are attached, optionally form a cyclic moiety, and that $R^3$ and $R^4{}_1$, optionally form a keto or, with the carbon atom to which they are attached, optionally form a cyclic moiety.

29 Claims, No Drawings

OTHER PUBLICATIONS

Medakovic, "An Efficient Synthesis of Methyl 1,2,3, 4–tetra–O–acetyl–β–L–Idopyranuronate", Carbohydrate Research 253:299–300, 1994.

Petitou et al., "First Synthetic Carbohydrates with the Full Anticoagulant Properties of Hepartin", Angew. Chem. Int. Ed. 37:3009–3013, 1998.

Rochepeau–Jobron et al., "Diastereoselective Hydroboration of Substituted Exo–glucals Revisited. A Convenient Route for the Preparation of L–iduronic Acid Derivatives", Carbohydrate Research 303:395–406, 1997.

Sinay et al., "Total Synthesis of a Heparin Pentasaccharide Fragment Having High Affinity for Antithrombin III", Carbohydrate Research 132:C5–C9, 1984.

Van Cleve et al., "A Practical Synthesis of 6–O–Methyl–D–Glucose", Carbohydrate Research 137:259–264, 1989.

Chida et al., "Total Synthesis of Antibiotic Hygromycin A", J. Org. Chem. 56:2976–2983, 1991.

Vlahov et al., "Regioselective Synthesis of Derivative of L–Idopyranuronic Acid: A Key Constituent of Glycosaminoglycans", Tetrahedron Letters 36:8379–8382, 1995.

* cited by examiner

METHODS OF PREPARING OPTICALLY PURE SUGARS

BACKGROUND OF THE INVENTION

Many biologically active molecules contain sugar moieties which are optically active. For example, mammalian glycoaminoglycans (e.g., heparin, heparan sulfates, and dermatan sulfate) and aminoglycoside antibiotics (e.g., neomycin B, paromomycin, and lividomycin A) all contain L-ido sugars. See Lindahl, *Pure & Appl. Chem.*, v. 69, 1897 (1997) and Fourmy et al., *Science* vol. 274, 1367 (1996). To facilitate the development of new therapeutic sugar-containing compounds, there is a need for simple methods of preparing optically pure sugars.

SUMMARY OF THE INVENTION

An aspect of this invention relates to a method of preparing a compound of formula (I):

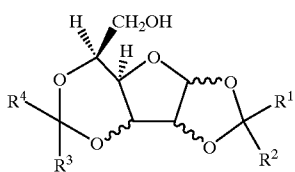

(I)

The method includes reacting a compound of formula (II):

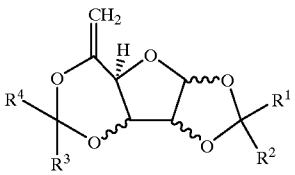

(II)

with a hydroborating reagent to form a borane-containing intermediate, and reacting the borane-containing intermediate with a hydroperoxide in a basic aqueous medium to form a compound of formula (I). Each of $R^1$, $R^2$, $R^3$, and $R^4$, independently, is hydrogen, alkyl, cycloalkyl, heterocycloalkyl, alkoxy, aryl, heteroaryl, aralkyl, heteroaralkyl, haloalkyl, or alkyloxyalkyl. Note that $R^1$ and $R^2$, together, can optionally form a keto or, together with the carbon atom to which they are attached, optionally form a cyclic moiety. Similarly, $R^3$ and $R^4$, together, can optionally form a keto or, together with the carbon atom to which they are attached, optionally form a cyclic moiety. The compound of formula (II) is prepared by reacting a compound of formula (III):

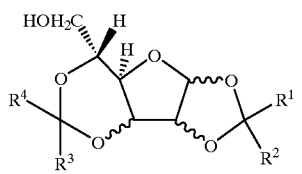

(III)

with a halogenating reagent to produce a halo-containing intermediate, and then reacting the halo-containing intermediate with a base to effect a double bond. As to the compound of formula (III), it is prepared by reacting a compound of formula (IV):

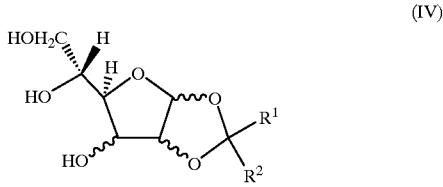

(IV)

with a ketal- or an acetal-forming reagent.

Alternatively, the compound of formula (II), supra, is prepared by reacting a compound of formula (V):

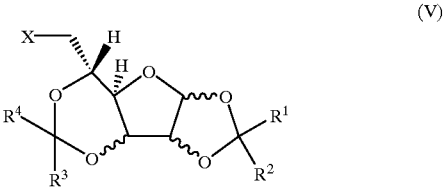

(V)

wherein X is halo, with a base to effect a double bond. The compound of formula (V) is prepared by reacting a compound of formula (VI):

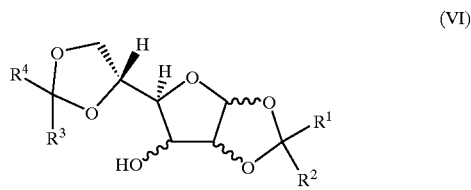

(VI)

with a halogenating reagent.

Another aspect of this invention relates to a method of preparing an 1,6-anhydro-L-ido sugar. The method includes reacting a compound of formula (II), supra, with a hydroborating reagent to form a borane-containing intermediate; reacting the borane-containing intermediate with a hydroperoxide in a basic aqueous medium to form a compound of formula (I); and deprotecting the compound of formula (I) in an acidic medium. In this method, the compound of formula (II) and the compound of formula (I) are 1,2-O-Y-3,5-O-Z-α-D-xylo-hex-5-enofuranoside and 1,2-O-Y-3,5-O-Z-β-L-idofuranoside, respectively, where Y is —C($R^1$)($R^2$)— and Z is —C($R^3$)($R^4$)—. Each of $R^1$, $R^2$, $R^3$, and $R^4_1$, independently, is hydrogen, alkyl, cycloalkyl, heterocycloalkyl, alkoxy, aryl, heteroaryl, aralkyl, heteroaralkyl, haloalkyl, or alkyloxyalkyl. Note that $R^1$ and $R^2$, together, can optionally form a keto or, together with the carbon atom to which they are attached, optionally form a cyclic moiety, and that $R^3$ and $R^4$, together, optionally form a keto or, together with the carbon atom to which they are attached, optionally form a cyclic moiety. For example, if each of $R^1$ and $R^2$ is a methyl, then —C($R^1$)($R^2$)— is a isopropylidene.

A method of preparing a salt of a compound of formula (I) is also within the scope of this invention. For example, a salt of such a compound can be formed between an amino substituent of the benzene ring of a benzylidene group and a negatively charged anion, e.g., chloride, bromide, iodide, sulfate, or nitrate.

It should be recognized that a method of this invention includes preparing any optical isomers of formula (I).

As used herein, alkyl is a straight or branched hydrocarbon chain containing 1 to 8 carbon atoms. Examples of alkyl include, but are not limited to, methyl, ethyl, propyl, isopropyl, butyl, isobutyl, sec-butyl, tert-butyl, n-pentyl, 2-methylpentyl, and 4-ethylhexyl. By cycloalkyl is meant a cyclic alkyl group containing 3 to 8 carbon atoms. Some examples of cycloalkyl are cyclopropyl, cyclopentyl, cyclohexyl, cycloheptyl, adamantyl, and norbornyl. Heterocycloalkyl is a cycloalkyl group containing 1–3 heteroatoms such as nitrogen, oxygen, or sulfur. Examples of heterocycloalkyl include piperidinyl, piperazinyl, tetrahydropyranyl, tetrahydrofuryl, and morpholinyl. As used herein, aryl is an aromatic group containing 6–12 ring atoms and can contain fused rings, which may be saturated, unsaturated, or aromatic. Examples of an aryl group include phenyl, naphthyl, biphenyl, phenanthryl, and anthracyl. Heteroaryl is aryl containing 1–3 heteroatoms such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl. A cyclic moiety is cycloalkyl, heterocycloalkyl, aryl, or heteroaryl. A cyclic moiety can also be fused rings and can be formed from two or more of the just-mentioned groups. An example of a cyclic moiety is phenanthryl.

An amino group can be unsubstituted, mono-substituted, or di-substituted. It can be substituted with groups such as alkyl, cycloalkyl, heterocycloalkyl, aryl, heteroaryl, aralkyl, or heteroaralkyl. Halo refers to fluoro, chloro, bromo, or iodo.

A hydroborating reagent refers to a reagent which transforms a double bond-containing compound to a borane-containing compound. Examples of such a hydroborating reagent include borane.tetrahydrofuran, borane.dimethyl sulfide, disiamyl-borane, thexylborane, thexylchloroborane.dimethyl sulfide, and 9-borabicyclo[3.3.1]nonane. The borane-containing compound can then be oxidized to an alcohol by reacting with a hydroperoxide such as hydrogen peroxide or t-butyl peroxide.

A halogenating reagent reacts with and transforms a compound with a suitable functionality, e.g., a good leaving group such as halide, into a halo-containing compound via reactions such as nucleophilic substitution. A halogenating reagent can be a chlorinating, a brominating, or an iodinating reagent. Examples of such a reagent include hydrogen halides (e.g., HBr), thionyl chloride, N-bromosuccinimide, and methyl iodide. The halo-containing compound can undergo dehydrohalogenation to form a double bond-containing compound in the presence of a base such as 1,8-diazabicyclo[5.4.0]undec-7-ene, diisopropylethylamine, triethylamine, or dimethylpyridine.

A ketal- or an acetal-forming reagent protect a pair of neighboring diols as a cyclic ketal or acetal group. Some commonly used ketal- or acetal-forming group include butylidene acetal, isopropyliene ketal, ethylidene acetal, methylene acetal, cyclohexylidene ketal, benzylidene acetal, o-nitrobenzylidene acetal, and 2,4-dimethoxybenzylidene acetal. More ketal- or acetal-forming groups can be found in references such as Greene, T. W., *Protective Groups in Organic Synthesis*, John Wiley & Son, Inc., chapter 2 (1981).

Unless otherwise defined, all technical and scientific terms used herein have the same meaning as commonly understood by one of ordinary skill in the art to which this invention belongs. Although methods and materials similar or equivalent to those described herein can be used in the practice of the present invention, suitable methods and materials are described below. All publications mentioned herein are incorporated by reference in their entirety.

Other features or advantages of the present invention will be apparent from the following detailed description of several embodiments, and also from the appending claims.

DETAILED DESCRIPTION OF THE INVENTION

Compounds of formula (I) can be prepared in their optically pure form by two methods of this invention, which are illustrated in Schemes 1 and 2 below.

In the method shown in Scheme 1, 1,2-O-isopropylidene-α-D-glucofuranoside is used as an exemplary starting material. Selective benzylidene protection of 1,2-O-isopropylidene-α-D-glucofuranoside affords a primary alcohol, i.e., 3,5-O-benzylidene-1,2-O-isopropylidene-α-D-glucofuranoside (step a). Other ketal or acetal groups, e.g., isopropylidene or butylidene, can be used instead of benzylidene. Note that the benzylidene group restricts the relative position of the C5-C6 bond with respect to the C3-O4 bond. 3,5-O-Benzylidene-1,2-O-isopropylidene-α-D-glucofuranoside is then converted into the key intermediate, 3,5-O-benzylidene-1,2-O-isopropylidene-6-deoxy-α-D-xylo-hex-5-enofuranoside, by sequential Mitsunobu-type iodination and elimination of HI (step b). Other dehydrohalogenation methods for forming a double bond, e.g., dehydrochlorination or dehydrobromination, can also be used. Highly stereoselective hydroboration of 3,5-O-benzylidene-1,2-O-isopropylidene-6-deoxy-α-D-xylo-hex-5-enofuranoside with a suitable reagent and subsequent oxidation with a suitable hydroperoxide leads to the desired compound of formula (I), 3,5-O-benzylidene-1,2-O-isopropylidene-β-L-idofuranoside as the only diastereoisomer (step c). Examples of a suitable hydroborating reagent include borane.dimethyl sulfide, disiamylborane, thexylborane, thexylchloroborane.dimethyl sulfide, and 9-borabicyclo[3.3.1]nonane. Two examples of a suitable hydroperoxide are hydrogen peroxide and t-butylperoxide. Example 1 illustrates this method.

Scheme I

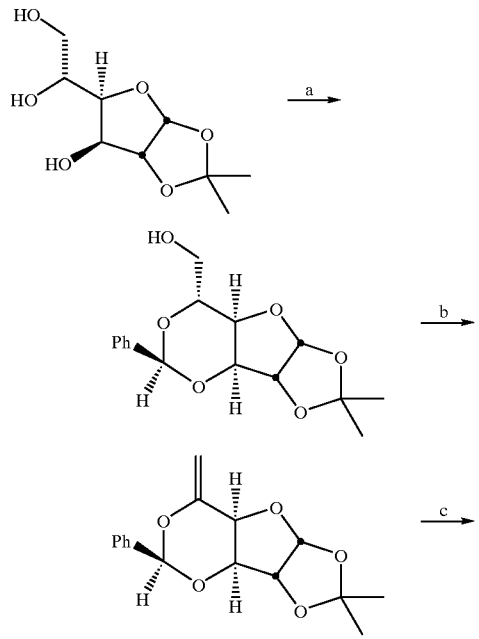

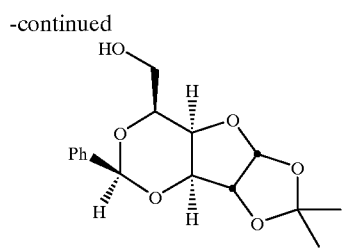

a) PhCHO, ZnCl₂, RT, 3h; b) 1. Ph₃P, DEAD, MeI, THF, 0° C. to RT, 19h; 2. DBU, toluene, 85° C., 12h; c) Borane/DMS, THF, RT, 2h; 30% H₂O₂, 3N NaOH, 30 min Another method is illustrated in Scheme 2 below. As an example, diacetone D-glucose is used as the starting material. Isopropylidene rearrangement and regioselective bromination of diacetone D-glucose take place simultaneously to produce 6-bromo-1,2:3,5-di-O-isopropylidene-α-D-glucofuranoside (step a). Similar to the method shown in Scheme 1 above, the ketal or acetal group protecting the 3- and 5-hydroxyl groups is not limited. The ketal and acetal group is used to restrict the relative position of the C5-C6 bond with respect to the C3-O4 bond. Note that the bromination step can be replaced by chlorination or iodination. Dehydrohalogenation of 6-bromo-1,2:3,5-di-O-isopropylidene-α-D-glucofuranoside produces the key intermediate, 1,2:3,5-di-O-isopropylidene-α-D-xylo-hex-5-enofuranoside (step b), which, upon hydroboration and oxidative work-up, is converted to the desired compound of formula (I), 1,2:3,5-di-O-isopropylidene-α-L-idofuranoside, as the single product (step c). Similar to the method described above, hydroboration and oxidation can be conducted in the presence of any suitable hydroborating reagent and hydroperoxide, e.g., borane.dimethyl sulfide and hydrogen peroxide, respectively. Example 2 illustrates this method.

Scheme 2

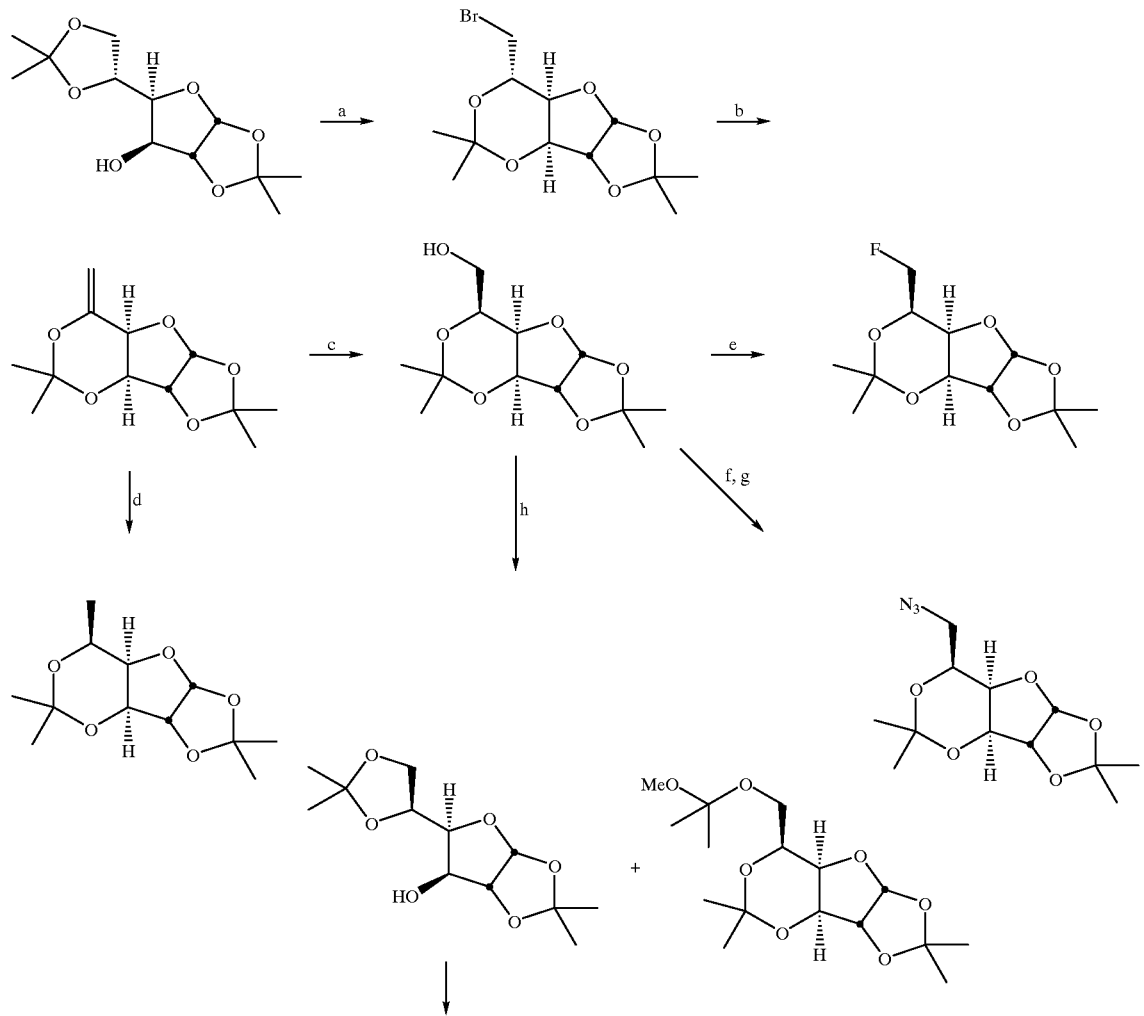

-continued

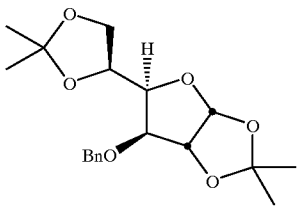

a) Ph₃P, NBS, DMF, 100° C., 3h; b) DBU, PhCH₃, 80° C., 16h; c) 1. BH₃/DMS, THF, RT, 2h; 2. 30% H₂O₂, 3N NaOH, 30 min; d) 10% Pd/C, EtOH, RT, 6h; e) DAST, CH₂Cl₂, -40° C to RT, 2h; f) TsCl, Pyr. RT, 6h; g) NaN₃, DMF, 90° C., 72h; h) cat. CSA, MeO(OMe)₂Me, acetone, RT, 5h; i) NaH, BnBr, DMF, 0° C. to RT, 16h Each of the methods shown in Schemes 1 and 2 above involves a similar key intermediate, i.e., 3,5-O-benzylidene-1,2-O-isopropylidene-6-deoxy-α-D-xylo-hex-5-enofuranoside and 1,2:3,5-di-O-isopropylidene-α-D-xylo-hex-5-enofuranoside; both being compounds of formula (II). As mentioned above, the 3,5-acetal or 3,5-ketal group restricts the relative position of the C5-C6 bond to the C3-O4 bond, and the whole molecule is kept in the form of a cis-anti-cis tricyclic fused compounds. This orientation induces high diastereoselectivity during hydroboration. More specifically, borane adds across the 5-exo-double bond of a compound of formula (II) from the less-hindered side, i.e., from the a-face, to avoid the bulky axial C4-O4 bond, thus forming the substituted group (CH₂OH) at the equatorial position of C5 (L-form). The effect of 3,5-acetal or 3,5-ketal group is further evidenced in the palladium-catalyzed hydrogenation of 1,2:3,5-di-O-isopropylidene-α-D-xylo-hex-5-enofuranoside (step d of Scheme 2). Similar to the hydroboration reaction, the addition of hydrogen in this reaction takes place at the less-hindered α-face of the molecule, and results in 6-deoxy-1,2:3,5-di-O-isopropylidene-α-L-idofuranoside as the only product. Example 3 illustrates this method.

Compounds of formula (I) can undergo further reactions to transform the functional groups attached thereon. For example, 1,2:3,5-di-O-isopropylidene-α-L-idofuranoside can react with (diethylamino)sulfur trifluoride (DAST) to afford 6-fluoro-6-deoxy-1,2:3,5-di-O-isopropylidene-β-L-idofuranoside (step e of Scheme 2). See Example 4 below. 1,2:3,5-di-O-isopropylidene-α-L-idofuranoside can also react with tosyl chloride (TsCl), and then with sodium azide to form 6-azido-1,2:3,5-di-O-isopropylidene-β-L-idofuranoside (steps f and g of Scheme 2). See Example 5 below. Example 6 below demonstrates that 1,2:3,5-di-O-isopropylidene-α-L-idofuranoside can undergo isopropylidene rearrangement in the presence of 2,2-dimethoxypropane and a catalytic amount of (±)-camphorsulfonic acid to afford 1,2:5,6-di-O-isopropylidene-α-L-idofuranoside (step h of Scheme 2), which can be used to synthesize L-talose and 3-functionalized-L-idose. See Brimacombe et al., *J. Chem. Soc.* C 1632 (1970). Example 7 below shows that benzylation of 1,2:5,6-di-O-isopropylidene-α-L-idofuranoside with sodium hydride and benzyl bromide leads to the corresponding 3-O-benzyl adduct (step i of Scheme 2), which is an important precursor for the synthesis of poly-functionalized heparin-liked molecules. See van Boeckel et al., *J. Carbohydr. Chem.* vol. 4, 293 (1985).

Compounds of formula (I) can also undergo arrangements after deprotecting of the ketal or acetal groups. For example, the acetal and ketal groups of 3,5-O-benzylidene-1,2-O-isopropylidene-6-deoxy-α-D-xylo-hex-5-enofuranoside and 1,2:3,5-di-O-isopropylidene-α-D-xylo-hex-5-enofuranoside can be deprotected in acidic medium, e.g., in diluted sulfuric acid, and rearranged to form 1,6-anhydro-β-L-idospyranoside. Further acetylation affords 1,6-anhydro-2,3,4-tri-O-acetyl-β-L-idospyranoside. See Examples 8 and 9 below. Deprotection and rearrangement of 3-O-benzyl-1,2:5,6-di-O-isopropylidene-β-L-idofuranose in an analogous manner produces 1,6-anhydro-3-O-benzyl-β-L-idopyranoside, which can then react with benzoyl chloride to afford 1,6-anhydro-3-O-benzyl-2-O-benzoyl-β-L-idopyranoside as the single regioisomer. See Examples 10 and 11 below.

The following specific examples, which describe syntheses of compounds of formula (I) and derivatives thereof, are to be construed as merely illustrative, and not limitative of the remainder of the disclosure in any way whatsoever.

EXAMPLE 1

Synthesis of 3,5-O-benzylidene-1,2-O-isopropylidene-α-D-glucofuranoside

To a mixture of 1,2-O-isopropylidene-α-D-glucofuranoside (3.0 g, 13.6 mmol) and anhydrous zinc chloride (4.0 g, 29.4 mmol) was added benzaldehyde (12.0 g, 114 mmol) at room temperature under nitrogen. The mixture was stirred for 4 hours, then diluted with ethyl acetate (EtOAc, 20 mL). The resulting solution was washed with water (2×40 mL), evaporated, and recrystallized from hexane at 0° C. to afford 3,5-O-benzylidene-1,2-O-isopropylidene-α-D-glucofuranoside (2.48 g, 56%) as a white solid. $^1$H NMR (300 MHz, CDCl₃) δ7.47 (m, 2H), 7.36 (m, 3H), 6.03 (d, 1H, J=3.6 Hz), 5.84 (s, 1H), 4.65 (d, 1H, J=3.6 Hz), 4.46 (d, 1H, J=2.2 Hz), 4.36 (dd, 1H, J=7.1, 4.5 Hz), 4.11 (d, 1H, J=2.2 Hz), 4.06 (ddd, 1H, J=11.6, 7.1, 4.5 Hz), 3.91 (ddd, 1H, J=11.6, 7.1, 4.5 Hz), 1.86 (dd, 1H, J=7.1, 3.6 Hz), 1.51 (s, 3H), 1.32 (s, 3H); $^{13}$C NMR (75 MHz, CDCl₃) δ137.5 (C), 129.3 (CH), 128.3 (CH), 126.2 (CH), 111.9 (C), 104.9 (CH), 94.4 (CH), 83.8 (CH), 78.0 (CH), 74.0 (CH), 72.9 (CH), 61.9 (CH₂), 26.6 (CH₃), 26.0 (CH₃).

Synthesis of 6-iodo-3,5-O-benzylidene-1,2-O-isopropylidene-α-D-glucofuranoside

To a solution of 3,5-O-benzylidene-1,2-O-isopropylidene-α-D-glucofuranoside (1.35 g, 4.37 mmol) and triphenylphosphine (1.72 g, 6.55 mmol) in tetrahydrofuran (THF, 6.0 mL) was added a solution of diethyl azodicarboxylate (1.1 mL, 6.12 mmol) in THF (5.0 mL) and methyl iodide (0.5 mL, 6.33 mmol) was added at 0° C. under nitrogen. The mixture was gradually warmed up and stirred at room temperature for 19 hours. The reaction was quenched with saturated NaHCO₃ (aq), and the mixture was extracted with EtOAc (3×10 mL). The combined organic layers were washed with brine, dried over MgSo₄, filtered, evaporated, and purified by column chromatography using EtOAc/Hex (1/10) as eluent to afford the iodo-compound (1.37 g, 75%) as a white solid. $[\alpha]^{25}{}_D=23°$ (c=1, CHCl$_3$); MP=135–136° C.; IR (CHCl$_3$) 2996 (s), 2953 (m), 2914 (s), 1435 (m), 1386 (s), 1215 (s), 1173 (s), 1008 (s), 885 (s), 757 (s), 700 (s) cm$^{-1}$; $^1$H NMR (300 MHz, CDCl$_3$) $\delta$7.50 (m, 2H), 7.37 (m, 3H), 6.06 (d, 1H, J=3.5 Hz), 5.66 (s, 1H), 4.67 (d, 1H, J=3.5 Hz), 4.45 (d, 1H, J=2.3 Hz), 4.44 (t, 1H, J=7.6 Hz), 4.28 (dd, 1H, J=2.3 Hz), 3.51 (ddd, 2H, J=14.3, 10.8, 7.6 Hz), 1.54 (s, 3H), 1.35 (s, 3H); $^{13}$C NMR (75 MHz, CDCl$_3$) $\delta$136.9 (C), 128.9 (CH), 128.0 (CH), 125.9 (CH), 111.8 (C), 104.9 (CH), 92.3 (CH), 83.2 (CH), 76.5 (CH), 73.2 (CH), 73.1 (CH), 29.4 (CH$_2$), 26.6 (CH$_3$), 26.0 (CH$_3$); EIMS m/z (relative intensity) 418 (M$^+$, 5), 403 (10), 248 (8), 142 (42), 113 (100), 77 (18), 59 (19), 43 (49); HRMS calcd for C$_{16}$H$_{19}$O$_5$I (M$^+$) 418.0269, Found 418.2308; Anal. calcd for C$_{16}$H$_{19}$O$_5$I: C, 45.95; H, 4.58; O, 19.13; I, 30.34. Found: C, 46.08; H, 4.62.

Synthesis of 3,5-O-benzylidene-1,2-O-isopropylidene-6-deoxy-α-D-xylo-hex-5-enofuranoside To a solution of 6-iodo-3,5-O-benzylidene-1,2-O-isopropylidene-α-D-glucofuranoside (2.45 g, 5.85 mmol) in toluene (18 mL) was added 1,8-diazabicyclo[5.4.0]undec-7-ene (DBU, 1.8 mL, 11.71 mmol) at room temperature under nitrogen. The mixture was warmed up to 85° C. for 12 hours. After cooling down to room temperature, the mixture was diluted with EtOAc (20 mL) and the resulting solution was washed with 1 M H$_2$SO$_4$ (aq), saturated NaHCO$_3$ (aq), water, and brine. The organic layer was dried over MgSO$_4$, filtered, evaporated, and purified by column chromatography using EtOAc/Hex (1/8) as eluent to afford the titled compound (1.57 g, 92%) as a white solid. $[\alpha]^{25}{}_D=61°$ (c=1, CHCl$_3$). MP=126–127° C.; IR (CHCl$_3$) 3118 (w), 3066 (w), 2992 (m), 2921 (m), 2877 (m), 2849 (w), 1663 (m), 1459 (m), 1400 (m), 1080 (s), 1002 (s), 885 (s), 757 (s), 700 (s) cm$^{-1}$; $^1$H NMR (300 MHz, CDCl$_3$) $\delta$7.50 (m, 2H), 7.37 (m, 3H), 6.04 (d, 1H, J=3.7 Hz), 5.54 (s, 1H), 4.93 (d, 1H, J=1.2 Hz), 4.78 (d, 1H, J=1.2 Hz), 4.67 (d, 1H, J=3.7 Hz), 4.50 (d, 1H, J=2.3 Hz), 4.42 (d, 1H, J=2.3 Hz), 1.54 (s, 3H), 1.32 (s, 3H); $^{13}$C NMR (75 MHz, CDCl$_3$) $\delta$152.6 (C), 136.5 (C), 129.5 (CH), 128.3 (CH) 126.2 (CH), 112.0 (C), 105.4 (CH), 101.5 (CH$_2$), 100.2 (CH), 83.5 (CH), 80.2 (CH), 73.0 (CH), 26.7 (CH$_3$), 26.1 (CH$_3$); LRMS (EI, m/z %) 290 (M$^+$, 10), 275 (28), 247 (12), 129 (30), 113 (54), 104 (100), 77 (23), 59 (22), 43 (76); HRMS (FAB, M$^+$) calcd for C$_{16}$H$_{18}$O$_5$ 290.3189, Found 290.1154; Anal. calcd for C$_{16}$H$_{18}$O$_5$: C, 66.20; H, 6.25. Found: C, 66.23; H, 6.22.

Synthesis of 3,5-O-benzylidene-1,2-O-isopropylidene-β-L-idofuranoside

To a solution of 3,5-O-benzylidene-1,2-O-isopropylidene-6-deoxy-α-D-xylo-hex-5-enofuranoside (0.50 g, 1.73 mmol) in THF (8.5 mL) was added a 1M solution of borane. THF complex in THF (3.5 mL, 3.5 mmol) at room temperature under nitrogen. The mixture was stirred for 3 hours, followed by oxidative work-up with a mixture 30% H$_2$O$_2$ (5.2 mL) and 3 M NaOH (aq) (3.7 mL) at 0° C. The resulting solution was warmed up to 40° C. for 30 minutes. After cooling down to room temperature, the mixture was extracted with EtOAc (3×10 mL) and the combined organic layers were washed with brine, dried over MgSO$_4$, filtered, evaporated, and purified by column chromatography using EtOAc/Hex (1/2) as eluent to afford 3,5-O-benzylidene-1,2-O-isopropylidene-β-L-idofuranoside (0.48 g, 90%) as a white solid. $[\alpha]^{25}{}_D=4°$ (c=1, CHCl$_3$); MP=115–116° C.; IR (CHCl$_3$) 3290 (br), 2980 (w), 2913 (m), 2854 (w), 1745 (w), 1457 (w), 1405 (w), 1370 (m), 1146 (s), 1100 (s), 1014 (s), 885 (s), 757 (s), 700 (s) cm$^{-1}$; $^1$H NMR (300 MHz, CDCl$_3$) $\delta$7.48 (m, 2H), 7.38 (m, 3H), 6.02 (d, 1H, J=3.6 Hz), 5.52 (s, 1H), 4.62 (d, 1H , J=3.6 Hz), 4.41 (d, 1H, J=1.5 Hz), 4.14 (m, 2H), 3.99 (dd, 1H, J=11.9, 7.1 Hz,), 3.86 (d, 1H, J=11.9, 7.2 Hz), 2.52 (s, 1H), 1.52 (s, 3H), 1.32 (s, 3H); $^{13}$C NMR (75 MHz, CDCl$_3$) $\delta$137.2 (C), 129.2 (CH), 128.2 (CH), 126.1 (CH), 112.0 (C), 105.6 (CH), 99.4 (CH), 82.9 (CH), 79.5 (CH), 76.5 (CH), 72.3 (CH), 62.6 (CH$_2$), 26.6 (CH$_3$), 26.0 (CH$_3$); LRMS (EI, m/z %) 308 (M$^+$, 8), 293 (16), 277 (12) , 187 (8), 149 (10), 129 (32), 100 (100), 77 (44), 59 (30) 43 (90); HRMS (FAB, M$^+$) calcd for C$_{16}$H$_{20}$O$_6$ 308.3342, found 308.1258; Anal. calcd for C$_{16}$H$_{20}$O$_6$: C, 62.33; H, 6.54. Found: C, 62.28; H, 6.60.

EXAMPLE 2

Synthesis of 1,2:3,5-di-O-isopropylidene-α-D-xylo-hex-5-enofuranoside

To a solution of diacetone D-glucose (2.01 g, 7.72 mmol) and PPh$_3$ (3.75 g, 14.3 mmol) in anhydrous dimethylformamide (20 mL) was added N-bromosuccinimide (2.0 g, 11.2 mmol) in small portions (4×500 mg). The mixture is warmed up in an oil bath at 100° C. for 3 hours. After cooling down to room temperature, the resulting solution was neutralized with saturated NaHCO$_3$ aqueous solution and the mixture was extracted with hexane (3×100 mL). The combined organic layers were washed with brine, dried over MgSO$_4$, and concentrated to ca. 20 mL. This mixture was added DBU (1.0 mL, 6.4 mmol) and the whole solution was refluxed for 6 hours. After cooling down to room temperature, the solvent was evaporated under reduced pressure and the residue was purified by column chromatography over 100 mL silica gel using EtOAc/hexane (1/9) as eluent to give 1,2:3,5-di-O-isopropylidene-α-D-xylo-hex-5-enofuranoside (1.13 g, 60%) as a colorless oil. $[\alpha]^{25}{}_D=163.7°$ (c 1.0, CHCl$_3$); IR (CHCl$_3$) 2988, 1660, 1375, 1082, 1017 cm$^{-1}$; $^1$H NMR (400 MHz, CDCl$_3$) $\delta$5.98 (d, J=3.7 Hz, 1H, H-1), 4.76 (d, J=0.6 Hz, 1H, H-6), 4.69 (d, J=0.8 Hz, 1H, H-6), 4.56 (d, J=3.7 Hz, 1H, H-2), 4.37 (d, J=2.3, Hz, 1H, H-3), 4.34 (d, J=2.3 Hz, 1H, H-4), 1.52 (s, 3H, methyl), 1.47 (s, 3H, methyl), 1.40 (s, 3H, methyl), 1.33 (s, 3H, methyl); $^{13}$C NMR (75 MHz, CDCl$_3$) $\delta$150.33, 111.79, 105.21, 101.36, 100.53, 84.27, 74.66, 72.34, 28.01, 26.72, 26.11, 21.90; HRMS (FAB, M$^+$) calcd for C$_{12}$H$_{18}$O$_5$ 242.1154, found 242.1152.

Synthesis of 1,2:3,5-di-O-isopropylidene-β-L-idofuranoside

To a solution of 1,2:3,5-di-O-isopropylidene-α-D-xylo-hex-5-enofuranose (1.44 g, 5.95 mmol) in anhydrous THF (15 mL) was added a 2M solution of borane-methyl sulphide complex in THF (3 mL, 6.0 mmol ) at room temperature under nitrogen. The mixture was stirred for 2 hours followed by oxidative treatment with a mixture of 35% H$_2$O$_2$ (3 mL) and NaOH (3 M, 3 mL) at 4° C. The resulting solution was warmed at 40° C. for 30 minutes and cooled back to room temperature. The reaction mixture was extracted with EtOAc (3×20 mL). The combined organic layers were washed with brine, dried over MgSO$_4$, and concentrated in vacuo. The residue was purified by column chromatogaraphy over 75 mL silica gel using EtOAc/hexane (2/3) as eluent to afford 1,2:3,S-di-O-isopropylidene-β-L-idofuranoside (1.3 g, 90%) as a colorless oil. $^1$H NMR (400 MHz, CDCl$_3$) $\delta$5.94 (d, J=3.7 Hz, 1H, H-1), 4.49 (d, J=3.7

Hz, 1H, H-2), 4.31 (d, J=2.2 Hz, 1 H, H-3), 4.12 (m, 1H, H-5), 4.01 (t, J=2.2 Hz, 1H, H-4), 3.88 (dd, J=11.6, 6.9 Hz, 1H, H-6), 3.78 (dd, J=11.6, 4.6 Hz, 1H, H-6), 1.48 (s, 3H, methyl), 1.44 (s, 3H, methyl), 1.40 (s, 3H, methyl), 1.31 (s, 3H, methyl).

EXAMPLE 3

Synthesis of 6-deoxy-1,2:3,5-di-O-isopropylidene-β-L-idofuranoside

To a solution of 1,2:3,5-di-O-isopropylidene-α-D-xylo-hex-5-enofuranose (100 mg, 0.41 mmol) in ethanol (6 mL), which was prepared according to the procedure described above, was added a catalytic amount of 10% Pd/C (10 mg). The mixture was bubbled with argon for 10 minutes, followed by the supplement of a hydrogen balloon for 6 hours. The resulting solution was filtered through celite, then washed with ethanol. The filtrate was concentrated in vacuo and the residue was purified by column chromatography with 20 mL silica gel using EtOAc/hexane (1/20) as eluent to afford the titled compound as a colorless oil (93 mg, 92%). $[\alpha]^{25}_D$=1.6° (c 1.0, $CHCl_3$); IR ($CHCl_3$) 2990, 1374, 1256, 1204, 1164, 1090, 1016 $cm^{-1}$; $^1H$ NMR (400 MHz, $CDCl_3$) δ5.89 (d, J=3.6 Hz, 1H, H-1), 4.43 (d, J=3.6 Hz, 1H, H-2), 4.12 (d, J=1.5 Hz, 1H, H-3), 4.07 (dq, J=6.5, 1.5, Hz, 1H, H-5), 3.78 (t, J=1.5 Hz, 1H, H-4), 1.42 (s, 3H, methyl), 1.37 (s, 3H, methyl), 1.32 (s, 3H, methyl), 1.27 (d, J=6.5 Hz, 3H, methyl), 1.25 (s, 3H, methyl); $^{13}C$ NMR (75 MHz, $CDCl_3$) δ111.44, 104.86, 97.90, 84.19, 73.85, 73.69, 64.48, 29.30, 26.62, 26.07, 19.09, 17.56 ; HRMS (FAB, $MH^+$) calcd for $C_{12}H_{21}O_5$ 245.1388, found 245.1381.

EXAMPLE 4

Synthesis of 6-fluoro-6-deoxy-1,2:3,5-di-O-isopropylidene-β-L-idofuranoside

To a solution of 1,2:3,5-di-O-isopropylidene-β-L-idofuranose (150 mg, 0.58 mmol) in anhydrous dichloromethane (4 mL) was added (diethylamino)sulfur trifluoride (0.47 ml 3.5 mmol) at −40° C. under nitrogen. After the cooling bath was removed, the mixture was gradually warmed up to room temperature and kept stirring for 6 hours. The resulting solution was cooled to −10° C. followed by addition of MeOH (2 mL) and then concentrated under vacuo. Chromatography over 30 mL of silica gel with EtOAc/hexane (1/9) as eluent to afforded the titled compound (83 mg, 55%) as a white solid. $[\alpha]^{25}_D$=4.20° (c 1.0, $CHCl_3$); IR ($CHCl_3$) 2991, 1375, 1204, 1163, 1016 $cm^{-1}$; $^1H$ NMR (400 MHz, $CDCl_3$) δ5.94 (d, J=3.6 Hz, 1H, H-1), 4.66 (ddd, J=48.2, 9.8, 4.2 Hz, 1H, H-6), 4.55 (ddd, J=48.2, 7.0, 4.2 Hz, 1H, H-6), 4.50 (d, J=3.6 Hz, 1H, H-2), 4.37–4.30 (m, 2H, H-3, H-5), 3.96 (t, J=2.0 Hz, 1H, H-4), 1.45 (s, 3H, methyl), 1.44 (s, 3H, methyl), 1.39 (s, 3H, methyl), 1.29 (S, 3H, methyl); $^{13}C$ NMR (75 MHz, $CDCl_3$) δ111.84, 105.30, 98.21, 85.00, 83.81, 81.65, 73.74, 70.69, 70.54, 68.10, 67.67, 29.03, 26.65, 26.09, 19.06; Anal. calcd for $C_{12}H_{20}O_5F$: C, 54.96; H, 7.25; found: C, 54.89; H, 7.36.

EXAMPLE 5

Synthesis of 6-azido-6-deoxy-1,2:3,5-di-O-isopropylidene-β-L-idofuranoside

To a solution of 1,2:3,5-di-O-isopropylidene-β-L-idofuranoside (150 mg, 0.58 mmol) in anhydrous pyridine was added tosyl chloride (121 mg, 0.63 mmol) at room temperature under nitrogen. After 4 hours, the mixture was diluted with EtOAc (15 mL) and the resulting solution was washed with 2 N HCl, saturated $NaHCO_3$ aqueous solution, water, and brine. The mixture was dried over anhydrous $MgSO_4$ and concentrated in vacuo to afford the crude 6-tosyl-1,2:3,5-di-O-isopropylidene-β-L-idofuranoside (210 mg, 88%). To a solution of the crude tosyl-compound in DMF (15 mL) was added $NaN_3$ (165 mg, 2.54 mmol). The mixture was heated at 90° C. for 72 hours, then cooled down to room temperature. The reaction mixture was diluted with EtOAc (20 mL) and the solution was washed with water twice, brine, dried over anhydrous $MgSO_4$ and concentrated in vacuo. The residue was purified by column chromatography over 30 mL silica gel with EtOAc/henxane (1/9) as eluent to afford the titled compound (121 mg, 74% in two steps) as a white solid. $[\alpha]^{25}_D$=7.3° (c 1.1, $CHCl_3$); IR ($CHCl_3$) 2925, 2101,1374, and 1088 $cm^{-1}$; $^1H$ NMR (400 MHz, $CDCl_3$) δ5.93 (d, J=3.6 Hz, 1H, H-1), 4.49 (d, J=3.6 Hz, 1H, H-2), 4.31 (d, J=2.2 Hz, 1H, H-3), 4.14 (ddd, J=8.1, 4.5, 2.2, Hz, 1H, H-5), 3.92 (t, J=2.2 Hz, 1H, H-4), 3.58 (dd, J=12.8, 8.1 Hz, 1H, H-6), 3.36 (dd, J=12.8, 4.5 Hz, 1H, H-6), 1.48 (s, 3H, methyl), 1.45 (s, 3H, methyl), 1.40 (s, 3H, methyl), 1.31 (s, 3H, methyl); $^{13}C$ NMR (75 MHz, $CDCl_3$) δ111.82, 105.14, 98.31, 83.91, 73.80, 71.33, 68.29, 51.72, 28.98, 26.63, 26.08,19.07; HRMS (FAB, $MH^+$) calcd for $C_{12}H_{20}O_5N_3$ 286.1402, Found 286.1405.

EXAMPLE 6

Synthesis of 1,2:5,6-di-O-isopropylidene-β-L-idofuranoside

To a solution of 1,2:3,5-di-O-isopropylidene-β-L-idofuranoside (300 mg, 1.15 mmol) in acetone (5 mL) was added 2,2-dimethoxypropane (1.0 mL, 11.3 mmol) and catalytic amount of camphorsulphonic acid (10 mg) at room temperature under nitrogen. The mixture was stirred for 6 hours and was quenched with triethylamine (1 mL). The resulting solution was evaporated in vacuo and the residue was purified by chromatography over 45 mL of silica gel using a gradient 10% to 40% EtOAc in hexane to afford the titled compound (126 mg, 42%) as a white solid, a side product 6-(1-methoxy-1-methylethoxy)-1,2:3,5-di-O-isopropylidene-β-L-idofuranoside (74 mg, 15%) as a colorless oil, and starting material 1,2:3,5-di-O-isopropylidene-β-L-idofuranoside (111 mg, 37% as a colorless oil. 1,2:5,6-Di-O-isopropylidene-β-L-idofuranoside: $^1H$ NMR (400 MHz, $CDCl_3$) δ5.94 (d, J=3.6 Hz, 1H, H-1), 4.45–4.48 (m, 2H), 4.22 (m, 3-OH), 4.12–4.06 (m, 3H), 3.7 (d, J=3.3 Hz, 1H), 1.47 (s, 3H, methyl), 1.45 (s, 3H, methyl), 1.42 (s, 3H, methyl), 1.29 (s, 3H, methyl); $^{13}C$ NMR (75 MHz, $CDCl_3$) δ111.65, 110.38, 104.86, 85.19, 78.02, 76.36, 74.74, 66.09, 26.74, 26.13, 25.83, 25.67. 6-(1-Methoxy-1-methylethoxy)-1,2:3,5-di-O-isopropylidene-β-L-idofuranoside: $^1H$ NMR (400 MHz, $CDCl_3$) δ5.59 (d, J=3.7 Hz, 1H, H-1), 4.48 (d, J=3.7 Hz, 1H, H-2), 4.29 (d, J=2.1 Hz, 1H, H-3), 4.18 (t, J=2.1 Hz, 1H, H-4), 4.14 (dt, J=6.1, 1.9 Hz, 1H, H-5), 3.71 (dd, J=9.7, 6.0 Hz, 1H, H-6), 3.56 (dd, J=9.7, 6.3 Hz, 1H, H-6), 3.22 (s, 3H, $OCH_3$), 1.48 (s, 3H, methyl), 1.46 (s, 3H, methyl), 1.39 (s, 3H, methyl), 1.35 (s, 6H, 2 methyl), 1.32 (s, 3H, methyl); $^{13}C$ NMR (75 MHz, $CDCl_3$) δ111.60, 105.12, 100.09, 98.11, 84.04, 73.81, 71.44, 68.31, 61.10, 48.54, 29.18, 26.67, 26.22, 24.40, 19.18.

EXAMPLE 7

Synthesis of 3-O-benzyl-1,2:5,6-di-O-isopropylidene-β-L-idofuranose

To a solution of 1,2:5,6-di-O-isopropylidene-β-L-idofuranose (200 mg, 0.77 mmol) in DMF (2 mL) was added benozyl bromide (0.11 ml, 0.92 mmol) at room temperature under nitrogen. The mixture was cooled in an ice bath for 15 minutes, then treated with 60% sodium hydride (40 mg, 1.0 mmol). The reaction mixture was gradually warmed up to room temperature and kept stirring overnight. The reaction was quenched with water (6 mL) and the aqueous portion was extracted with EtOAc (3×10 mL). The combined organic layers were washed with brine, dried over anhydrous $MgSO_4$, filtered and concentrated in vacuo. The residue was purified by column chromatography over 20 mL silica gel with EtOAc/hexane (1/9) as eluent to give the titled compound (248 mg, 92%) as a colorless oil. $^1$H NMR (400 MHz, $CDCl_3$) δ7.37–7.29 (m, 5H, Ph), 5.98 (d, J=3.8 Hz, 1H, H-1), 4.66, 4.44 (ABq, J=11.8 Hz, 2H, $PhCH_2$), 4.61 (d , J=3.8 Hz, 1H, H-2), 4.38 (d, J=7.9 Hz, 1H), 4.14 (dd, J=8.2, 3.6 Hz, 1H), 3.90 (dd, J=8.2, 6.6 Hz, 1H), 3.85 (d, J=3.6 Hz, 1H), 3.42 (dd, J=8.2, 7.4 Hz, 1H), 1.50 (s, 3H, methyl), 1.43 (s, 3H, methyl), 1.36 (s, 3H, methyl), 1.34 (s, 3H, methyl); $^{13}$C NMR (75 MHz, $CDCl_3$) δ136.70, 128.58, 128.24, 128.03, 111.83, 109.75, 105.45, 82.29, 81.94, 81.80, 74.99, 71.56, 65.65, 26.85, 26.76, 26.34, 25.30.

EXAMPLE 8

Synthesis of 1,6-anhydro-2,3,4-tri-O-acetyl-β-L-idospyranoside

To a solution of 3,5-O-benzylidene-1,2-O-isopropylidene-β-L-idofuranoside (90 mg, 0.29 mmol) in 0.1 M $H_2SO_4$ aqueous solution (2 mL) was heated at 100° C. for 16 hours. After cooling down to room temperature, the reaction was quenched by $NaHCO_3$ solid (200 mg) and the mixture was co-evaporated with ethanol followed by toluene in vacuo to afford a white solid. To a solution of this white solid in pyridine (1 mL) was added acetic anhydride (0.5 mL) at room temperature under nitrogen. The mixture was stirred for 12 hours and quenched with water (5 mL). The aqueous portion was extracted with EtOAc (3×10 mL) and the combined organic layers were washed with 0.1 N HCl(aq) twice, saturated $NaHCO_3$(aq), water, and brine. The separated organic layer was dried over $MgSO_4$, filtered, evaporated, and purified by column chromatography using EtOAc/Hex (2/3) as eluent to afford the titled compound (60 mg, 72%) as a colorless oil. $^1$H NMR (300 MHz, $CDCl_3$) δ5.43 (d, 1H, J=1.6 Hz), 5.30 (t, 1H, J=8.4 Hz), 5.06 (dd, 1H, J=8.4, 4.6 Hz), 4.82 (dd, 1H, J=8.4, 1.6 Hz), 4.58 (t, 1H, J=4.6 Hz), 4.15 (d, 1H, J=8.2 Hz), 3.77 (dd, 1H, J=8.2, 4.6 Hz), 2.05 (s, 3H), 2.01 (s, 3H), 1.99 (s, 3H); $^{13}$C NMR (75 MHz, $CDCl_3$) δ170.1 (C), 169.8 (C), 99.1 (CH), 73.9 (CH), 72.6 (CH), 70.5 (CH), 70.4 (CH), 65.6 (CH), 20.6 ($CH_3$); LRMS (EI, m/z %) 289 (M+1, 52), 273 (8), 259 (6), 245 (8), 229 (32), 169 (18), 159 (100), 137 (94), 120 (15); HRMS (FAB, $MH^+$) calcd for $C_{12}H_{17}O_8$ 289.2645, found 289.0923.

EXAMPLE 9

Synthesis of 1,6-anhydro-2,3,4-tri-O-acetyl-β-L-idospyranoside

The synthesis of the titled compound from 1,2:3,5-di-O-isopropylidene-β-L-idofuranoside (103 mg, 0.4 mmol) is carried out according to the procedure described in Example 8 to afford the adduct (108 mg) in 92% yield.

EXAMPLE 10

Synthesis of 1,6-anhydro-3-O-benzyl-β-L-idopyranoside

The synthesis of the titled compound from 3-O-benzyl-1,2:5,6-di-O-isopropylidene-β-L-idofuranose (200 mg, 0.57 mmol) is carried out according to the procedure described in Example 8 to afford the product (108 mg, 75%) as a white solid. Mp 158–159° C.; $[α]^{27}_D$=65.8° (c 1.1, MeOH); IR ($CHCl_3$) 3301, 1135, 1063, 1028, 956 $cm^{-1}$; $^1$H NMR (400 MHz, $CDCl_3$) δ7.29–7.38 (m, 5H, Ph), 5.29 (d, J=1.9 Hz, 1H, H-1), 4.95, 4.74 (ABq, J=11.7 Hz, 2H, $PhCH_2$), 4.31 (t, J=4.6 Hz, 1H, H-5), 4.03 (d, J=7.7 Hz, 1H, H-6), 3.87 (m, 1H, H-2), 3.72 (m, 1H, H-4), 3.65 (m, 1H, H-3), 3.39 (t, J=7.7 Hz, 1H, H-6), 2.15 (d, J=3.0 Hz, 1H, 4-OH), 1.95 (d, J=8.9 Hz, 1H, 2-OH) ; $^{13}$C NMR (75 MHz, $CDCl_3$) δ138.40, 128.68, 128.03, 127.88, 101.82, 84.19, 75.44, 74.99, 74.50, 71.07, 65.05; HRMS (FAB, $M^+$) calcd for $C_{13}H_{16}O_5$ 252.0997, found 252.0992; Anal. calcd for $C_{13}H_{16}O_5$: C, 61.90; H, 6.30, found: C, 61.72 ; H, 6.18.

EXAMPLE 11

Synthesis of 1,6-anhydro-3-O-benzyl-2-O-benzoyl-β-L-idopyranoside

To a solution of 1,6-anhydro-3-O-benzyl-β-L-idopyranose (1.95 g, 7.74 mmol) in dichloromethane (20 mL) was added pyridine (2 mL, mmol) followed by addition of benzoyl chloride (0.95 mL, 8.12 mmol) at 0° C. under nitrogen. The mixture was stirred at 0° C. for 4 hours, then quenched with methanol (2 mL). The solution was evaporated and the residue was diluted with EtOAc (30 mL). The resulting solution was washed with 2 N HCl twice, saturated $NaHCO_3$ (aq), water, and brine. The separated organic layer was dried over anhydrous $MgSO_4$, and concentrated in vacuo. The residue was purified by re-crystallization using a solution of EtOAc/hexane (1/4) to afford the titled compound (2.2 g, 82%) as a white solid. $[α]^{27}_D$=127.50 (c 1.2, $CHCl_3$); MP 142–143° C.; IR ($CHCl_3$) 3473, 1722, 1272, 1113, 1027, 712 $cm^{-1}$; $^1$H NMR (400 MHz, $CDCl_3$) δ7.24–8.09 ( m, 10H, 2×Ph), 5.53 (d, J=1.6 Hz, 1H, H-1), 5.07 (dd, J=8.2, 1.6 Hz, 1H, H-2), 4.80, 4.65 (ABq, J=11.6 Hz, 2H, $PhCH_2$), 4.51 (t, J=4.5 Hz, 1H, H-5), 4.15 (d, J=7.5 Hz, 1H, H-6), 4.00 (m, 1H, H-4), 3.87 (t, J=8.2 Hz, 1H, H-3), 3.76 (dd, J=7,6, 5.1 Hz, 1H, H-6), 2.22 (d, J=3.0 Hz, 1H, 4-OH) ; $^{13}$C NMR (45 MHz, $CDCl_3$) δ165.76, 137.97, 133.40, 129.83, 129.45, 128.58, 128.47, 128.00, 127.67, 99.47, 80.29, 77.64, 75.06, 74.60, 71.37, 65.30; HRMS (FAB, $MH^+$) calcd for $C_{20}H_{20}O_6$ 357.1338; found 357.1353; Anal. calcd for $C_{20}H_{19}O_6$: C, 67.41; H, 5.61; found: C, 67.20; H, 5.44.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of preparing a compound of formula (I)

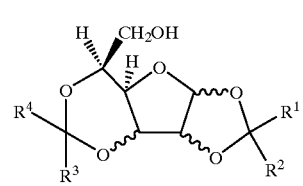

the method comprising:

reacting a compound of formula (II)

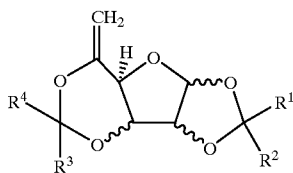

(II)

with a hydroborating reagent to form a borane-containing intermediate; and reacting the borane-containing intermediate with a hydroperoxide in a basic aqueous medium; wherein each of $R^1$, $R^2$, $R^3$, and $R^4$, independently, is hydrogen, alkyl, cycloalkyl, heterocycloalkyl, alkoxy, aryl, heteroaryl, aralkyl, heteroaralkyl, haloalkyl, or alkyloxyalkyl, provided that $R^1$ and $R^2$, optionally form a keto or, with the carbon atom to which they are attached, optionally form a cyclic moiety, and that $R^3$ and $R^4$, optionally form a keto or, with the carbon atom to which they are attached, optionally form a cyclic moiety.

2. The method of claim 1, wherein each of $R^1$, $R^2$, $R^3$, and $R^4$, independently, is hydrogen, alkyl, or aryl.

3. The method of claim 2, wherein the hydroborating reagent is borane.dimethyl sulfide.

4. The method of claim 2, wherein the hydroperoxide is hydrogen peroxide.

5. The method of claim 2, wherein each of $R^1$ and $R^2$, independently, is methyl, $R^3$ is phenyl, and $R^4$ is hydrogen.

6. The method of claim 5, wherein the hydroborating reagent is borane.dimethyl sulfide and the hydroperoxide is hydrogen peroxide.

7. The method of claim 1, wherein the compound of formula (I) is 3,5-O-benzylidene-1,2-O-isopropylidene-β-L-idofuranoside or 1,2:3,5-di-O-isopropylidene-β-L-idofuranoside.

8. The method of claim 1, wherein the compound of formula (II) is prepared by:

reacting a compound of formula (III)

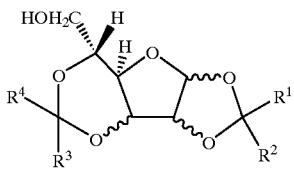

(III)

with a halogenating reagent to produce a halo-containing intermediate; and reacting the halo-containing intermediate with a base to effect a double bond.

9. The method of claim 8, wherein each of $R^1$, $R^2$, $R^3$, and $R^4$, independently, is hydrogen, alkyl, or aryl.

10. The method of claim 9, wherein each of $R^1$ and $R^2$, independently, is methyl, $R^3$ is phenyl, and $R^4$ is hydrogen.

11. The method of claim 10, wherein the halogenating reagent is methyl iodide and the base is 1,8-diazabicyclo[5.4.0]undec-7-ene.

12. The method of claim 8, wherein the compound of formula (II) is 3,5-O-benzylidene-1,2-O-isopropylidene-6-deoxy-α-D-xylo-hex-5-enofuranoside.

13. The method of claim 8, wherein the compound of formula (III) is prepared by reacting a compound of formula (IV)

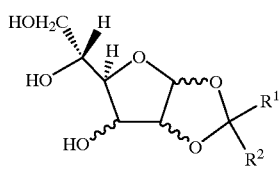

(IV)

with a ketal- or an acetal-forming reagent.

14. The method of claim 13, wherein each of $R^1$ and $R^2$, independently, is hydrogen, alkyl, or aryl.

15. The method of claim 14, wherein each of $R^1$ and $R^2$, independently, is methyl.

16. The method of claim 15, wherein the acetal-forming reagent is benzaldehyde.

17. The method of claim 13, wherein the compound of formula (III) is 3,5-O-benzylidene-1,2-O-isopropylidene-α-D-glucofuranoside.

18. The method of claim 1, wherein the compound of formula (II) is prepared by reacting a compound of formula (V)

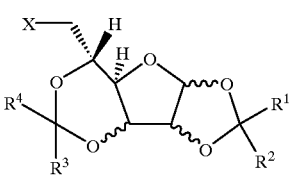

(V)

wherein X is halo, with a base to effect a double bond.

19. The method of claim 18, wherein X is chloro, bromo, or iodo.

20. The method of claim 19, wherein each of $R^1$, $R^2$, $R^3$, and $R^4$, independently, is hydrogen, alkyl, or aryl.

21. The method of claim 20, wherein X is bromo, each of $R^1$, $R^2$, $R^3$, and $R^4$, independently, is methyl, and the base is 1,8-diazabicyclo[5.4.0]undec-7-ene.

22. The method of claim 18, wherein the compound of formula (II) is 1,2:3,5-di-O-isopropylidene-α-D-xylo-hex-5-enofuranoside.

23. The method of claim 18, wherein the compound of formula (V) is prepared by reacting a compound of formula (VI)

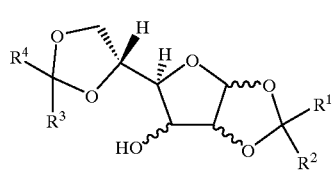

(VI)

with a halogenating reagent.

24. The method of claim 23, wherein each of $R^1$, $R^2$, $R^3$, and $R^4$, independently, is hydrogen, alkyl, or aryl.

25. The method of claim 24, wherein each of $R^1$, $R^2$, $R^3_{1}$, and $R^4$, independently, is methyl, and the halogenating reagent is bromosuccinimate.

26. The method of claim 23; wherein the compound of formula (V) is 6-bromo-1,2:3,5-di-O-isopropylidene-α-D-glucofuranoside.

27. A method of preparing an 1,6-anhydro-L-ido sugar comprising:

reacting a compound of formula (II)

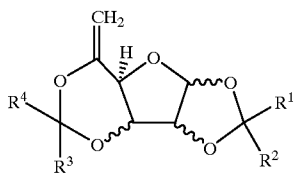

with a hydroborating reagent to form a borane-containing intermediate;

reacting the borane-containing intermediate with a hydroperoxide in a basic aqueous medium to form a compound of formula (I)

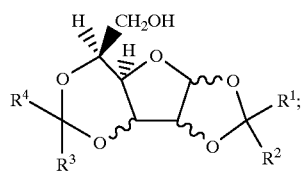

; and deprotecting the compound of formula (I) in an acidic medium; the compound of formula (II) being 1,2-O—Y-3,5-O—Z-6-deoxy-α-D-xylo-hex-5-enofuranoside and the compound of formula (I) being 1,2-O—Y-3,5-O—Z-β-L-idofuranoside where Y is —C($R^1$) ($R^2$)— and Z is —C($R^3$) ($R^4$)— in which each of $R^1$, $R^2$, $R^3$, and $R^4$, independently, is hydrogen, alkyl, cycloalkyl, heterocycloalkyl, alkoxy, aryl, heteroaryl, aralkyl, heteroaralkyl, haloalkyl, or alkyloxyalkyl, provided that $R^1$ and $R^2$, optionally form a keto or, with the carbon atom to which they are attached, optionally form a cyclic moiety, and that $R^3$ and $R^4$, optionally form a keto or, with the carbon atom to which they are attached, optionally form a cyclic moiety.

28. The method of claim 27, wherein each of $R^1$, $R^2$, $R^3$, and $R^4$, independently, is hydrogen, alkyl, or aryl.

29. The method of claim 28, wherein the compound of formula (II) is 3,5-O-benzylidene-1,2-O-isopropylidene-6-deoxy-α-D-xylo-hex-5-enofuranoside or 1,2:3,5-di-O-isopropylidene-α-D-xylo-hex-5-enofuranoside.

* * * * *